US011460403B2

(12) United States Patent
Akhavan-Tafti et al.

(10) Patent No.: US 11,460,403 B2
(45) Date of Patent: Oct. 4, 2022

(54) ELECTROLUMINESCENT METHODS AND DEVICES FOR CHARACTERIZATION OF BIOLOGICAL SPECIMENS

(71) Applicant: AhuraTech LLC, Brighton, MI (US)

(72) Inventors: Hashem Akhavan-Tafti, Brighton, MI (US); Ali Ghiaseddin, Howell, MI (US)

(73) Assignee: AhuraTech LLC, Brighton, MI (US)

( * ) Notice: Subject to any disclaimer, the term of this patent is extended or adjusted under 35 U.S.C. 154(b) by 567 days.

(21) Appl. No.: 16/530,086

(22) Filed: Aug. 2, 2019

(65) Prior Publication Data

US 2020/0011802 A1 Jan. 9, 2020

Related U.S. Application Data

(63) Continuation-in-part of application No. 16/376,643, filed on Apr. 5, 2019, which is a continuation-in-part
(Continued)

(51) Int. Cl.
*G01N 21/64* (2006.01)
*G01N 33/52* (2006.01)

(52) U.S. Cl.
CPC ......... *G01N 21/6456* (2013.01); *G01N 33/52* (2013.01)

(58) Field of Classification Search
None
See application file for complete search history.

(56) References Cited

U.S. PATENT DOCUMENTS 3,774,238 A 11/1973 Hardway, Jr.
4,434,657 A 3/1984 Matsumura et al.
(Continued)

FOREIGN PATENT DOCUMENTS

GB 2218812 A 11/1989
KR 101493310 B1 2/2015
(Continued)

OTHER PUBLICATIONS

Kumar et al. "A Review on Capacitive-Type Sensor for Measurement of Height of Liquid Level." Measurement and Control vol. 47(7). 2014. pp. 219-224.
(Continued)

*Primary Examiner* — Patrick Assouad
*Assistant Examiner* — Haidong Zhang
(74) *Attorney, Agent, or Firm* — Harness, Dickey & Pierce, P.L.C.

(57) ABSTRACT

Methods and devices for the characterization of biological specimens by the use of electroluminescent materials. When placed in close proximity or direct contact to a biological specimen and an electrical signal is transmitted, electroluminescence is generated in response to the presence of the specimen. The electroluminescence produced can be in the form of an image of the specimen. The image is captured by an optical device that collects light and displays or otherwise processes the image according to the particular need or purpose. In general, the method requires preparing an electroluminescent assembly including the biological specimen, a dielectric layer, and a substrate, put together in any order. The method uses an electrical signal transmitted to the assembly. The device may be configured in a closed-circuit electrical configuration or it may be in a configuration where the EL assembly is at open circuit with respect to the power source.

50 Claims, 5 Drawing Sheets

Related U.S. Application Data of application No. 16/027,471, filed on Jul. 5, 2018, application No. 16/530,086, filed on Aug. 2, 2019, which is a continuation-in-part of application No. 16/027,471, filed on Jul. 5, 2018.

(56) References Cited

U.S. PATENT DOCUMENTS

| | | | |
|---|---|---|---|
| 4,991,150 | A | 2/1991 | Wixom |
| 5,187,979 | A | 2/1993 | Edmark, III |
| 5,627,522 | A | 5/1997 | Walker et al. |
| 6,104,107 | A | 8/2000 | Avramenko et al. |
| 6,501,846 | B1 | 12/2002 | Dickinson et al. |
| 6,606,399 | B2 | 8/2003 | Burrows et al. |
| 6,630,307 | B2 | 10/2003 | Bruchez et al. |
| 6,823,731 | B1 | 11/2004 | Lin |
| 6,856,383 | B1 | 2/2005 | Vachris et al. |
| 7,008,559 | B2 | 3/2006 | Chen |
| 7,501,092 | B2 | 3/2009 | Chen |
| 8,810,778 | B2 | 8/2014 | Stautmeister et al. |
| 9,261,395 | B2 | 2/2016 | Shearer et al. |
| 9,741,948 | B2 | 8/2017 | Berger et al. |
| 10,084,042 | B2 | 9/2018 | Welch et al. |
| 10,241,111 | B2 | 3/2019 | Akhavan-Tafti et al. |
| 2002/0054696 | A1 | 5/2002 | Lee |
| 2003/0151735 | A1* | 8/2003 | Blumenfeld ....... G01N 21/6428 356/73 |
| 2004/0252867 | A1 | 12/2004 | Lan et al. |
| 2005/0059031 | A1* | 3/2005 | Bruchez ............ G01N 33/5014 435/6.12 |
| 2007/0095669 | A1 | 5/2007 | Lau et al. |
| 2009/0187357 | A1 | 7/2009 | Ho et al. |
| 2009/0206287 | A1 | 8/2009 | Trupke et al. |
| 2010/0097346 | A1 | 4/2010 | Sleeman |
| 2010/0105035 | A1 | 4/2010 | Hashsham et al. |
| 2010/0185064 | A1 | 7/2010 | Bandic et al. |
| 2011/0021970 | A1 | 1/2011 | Vo-Dinh et al. |
| 2013/0157895 | A1 | 6/2013 | Aimiya et al. |
| 2013/0298667 | A1 | 11/2013 | Bechtel et al. |
| 2013/0334960 | A1 | 12/2013 | Waffenschmidt et al. |
| 2014/0193841 | A1 | 7/2014 | Welch et al. |
| 2017/0089236 | A1 | 3/2017 | Andersen et al. |
| 2018/0132332 | A1 | 5/2018 | Akhavan-Tafti |

FOREIGN PATENT DOCUMENTS

| | | |
|---|---|---|
| KR | 20160011224 A | 1/2016 |
| WO | 200124586 A1 | 4/2001 |
| WO | 2005107818 A2 | 11/2005 |
| WO | 2017027643 A1 | 2/2017 |

OTHER PUBLICATIONS

Jiayuan Wang. "Liquid Level Sensing Using Capacitive-to-Digital Converters." Analog Dialogue 49-04. Apr. 2015.

Xiaoxhu Gao et al. "In vivo molecular and cellular imaging with quantum dots." Current Opinion in Biotechnology 2005. 16:63-72.

J. Aswathy et al. "Mn doped Zinc Sulphide nanocrystals for immunofluorescent labeling of epidermal growth factor receptors on cells and clinical tumor tissues." Nanotechnology 25 (2014) 445102.

F. Krujatz et al. Exploiting the Potential of OLED-Based Photo Organic Sensors for Biotechnological Applications. Chemical Sciences Journal. vol. 7, Issue 3. 2016.

Ying-Yu Ma et al. "Molecular Imaging of Cancer with Nanoparticle-Based Theranostic Probes." Hindawi. Contrast Media & Molecular Imaging. vol. 2017.

Congcong Mi et al. "Biosynthesis and characterization of CdS quantum dots in genetically engineered *Escherichia coli*." Journal of Biotechnology 153 (2011) 125-132.

Nako Nakatsuka et al. "Self-assembling peptide assemblies bound to ZnS nanoparticles and their interactions with mammalian cells." Colloids and Surfaces B: Biointerfaces 103 (2013) 405-415.

Stefan Niekamp et al. "Nanometer-accuracy distance measurements between fluorophores at the single-molecule level." PNAS. vol. 116, No. 10.

Anja Ostrowski et al. "Overview about the localization of nanoparticles in tissue and cellular context by different imaging techniques." Beilstein Journal of Nanotechnology. 2015, 6, 263-280.

Hiroshi Toda et al. "A Novel Immunohistochemical Staining Method Allows Ultrarapid Detection of Lymph Node Micrometastases While Conserving Antibody." Japan Society of Histochemistry and Cytochemistry 44(3): 133-139.

Jung Ho Yu et al. "High-resolution three-photon biomedical imaging using doped ZnS nanocrystals." Nature Materials. vol. 12.

Yu-Hong Cheng. "Plasmonic gold nanoparticles as multifaceted probe for tissue imaging." Chem Communication. 2019.

International Search Report and Written Opinion dated Oct. 24, 2019 regarding PCT/US2019/040256.

International Search Report completed on Feb. 14, 2022 regarding European Application No. 19830706.8.

\* cited by examiner

ELECTROLUMINESCENT METHODS AND DEVICES FOR CHARACTERIZATION OF BIOLOGICAL SPECIMENS

CROSS-REFERENCE TO RELATED APPLICATIONS

This application is a continuation-in-part of U.S. patent application Ser. No. 16/376,643, filed on Apr. 5, 2019, which is a continuation-in-part of U.S. application Ser. No. 16/027,471, filed on Jul. 5, 2018. This application is further a continuation-in-part of U.S. patent application Ser. No. 16/027,471, filed on Jul. 5, 2018. The entire disclosures of the above applications are incorporated herein by reference.

FIELD

The present disclosure is related to methods and devices used in characterizing a biological specimen by electroluminescence. The methods and devices may be used as a general staining methodology for visualization or analysis of cellular and tissue samples. The present methods and devices are suitable for use in microscopic investigations of biological specimens.

BACKGROUND

This section provides background information related to the present disclosure which is not necessarily prior art.

Photoluminescent (PL)-based analyte detection techniques are widely used in diagnostic and research laboratories. PL materials emit light upon photo-excitation. The basic instruments for monitoring PL emission of an analyte include a source of narrow-band radiation to excite the analyte, a means of selecting a narrow band of emission, and a detector.

Staining is a commonly used method for visualizing biological samples. Staining allows for enhancing contrast in a microscopic image of bulk tissues, cell populations, or organelles within individual cells. General and specific staining methods historically have relied on the use of highly colored staining materials to deposit onto particular classes of cellular substances or regions within cellular material. A commonly-used staining method of this type is H&E which, as the name suggests, uses two dyes including Haemotoxylin and Eosin. More recent methods using PL markers, such as dyes, have been developed and used for characterization and visualization of biological specimens. For instance, semiconductor nanostructures, in particular quantum dots (QDs) are used to prepare antibody-QD conjugates for in vivo tumor imaging and targeting. In general staining, fluorescent markers are used to indiscriminately stain components of a biological sample. Specific biological tissue staining includes immunohistochemistry (IHC) which involves binding between an antibody and an antigen in biological tissues. To visualize, a stained histologic specimen is often sandwiched between a glass microscope slide and coverslip and mounted on a light microscope stage.

Lasers are the most commonly-used source of narrow-band radiation for PL-based analyte detection. To address the high cost of and the harmful radiation from exposure to ultraviolet laser sources, electroluminescent light sources, such as light-emitting devices (LEDs), have become popular in developing diagnostic and biosensing systems. An electroluminescent (EL) device is defined as a device which emits photons in response to an electrical signal. EL devices allow the design of structurally integrated, miniaturized sensor arrays that provide low-cost, portable, and multi-analyte detection systems.

EL materials, such as zinc sulfide nanocrystals, require low input power to operate. They operate at high quantum efficiencies and emit within narrow bandwidths. EL materials are also often PL active. These features uniquely qualify EL materials for PL-based analyte detection and imaging. For instance, Aswathy et al. (2014; Nanotechnology) used manganese-doped ZnS nano-bioconjugates for direct labeling of clinical tumor tissues. Similarly, U.S. Pat. No. 10,241,111 further introduced the use of EL materials for assay characterization in liquid media. This disclosure further provides methods and devices for staining biological specimens using EL materials as markers. Methods and devices are known for visualizing biological specimens using EL devices as a general light source. U.S. Patent Application No. 20100105035A1 provides methods using an EL source for measuring PL in biological samples including PL imaging. Similarly, Krujatz et al. (2016; Chem Sci J) provides a thorough summary of methods and devices for using organic light-emitting devices (OLEDs) as excitation sources in analytical and biotechnological applications.

Antibodies can be utilized in order to provide detailed information regarding protein abundance, distribution and localization in a biological specimen, including tissue sections and cells. A biological specimen is processed via IHC or immunocytochemistry (ICC) techniques and labeled using chromogenic reagents or fluorescent labels, i.e., immunofluorescence (IF). IHC technique requires tissue samples to be embedded in paraffin or frozen to preserve tissue morphology, whereas ICC or staining involve shorter fixation period and are thus cheaper and faster to implement. Aswathy et al. (2014) used IF techniques to label cancer biomarkers. They particularly used Mn-doped ZnS nanocrystals to show their high specificity and accuracy on both cryopreserved and clinical tumor tissues. It was further discovered that the nanocrystal-labeled tissues were stable in various media and had a long (>15 months) shelf-life. Similarly, Yu et al. (2013; Nature Materials) showed that capped Mn:ZnS nanocrystals are physiologically stable and that their physical properties, including quantum efficiency and optical properties, are preserved in both serum and buffer solutions. Lastly, multiplexing is made possible with IHC.

ZnS nanocrystals can be further tuned to selectively target specific binding sites. For instance, Aswathy et al. (2014) showed that unconjugated cystine-capped Mn:ZnS nanocrystals can be directed to bind to targeted locations and then entirely washed off all other sites without any residues, therefore reducing the false positive signal. The examination of the stained tissue can be done via various detection methods including multi-photon spectroscopy (e.g., Yu et al. 2013; Nature Materials) or upconversion luminescence (e.g., Wei Chen 2005; U.S. Pat. Nos. 7,008,559, 7,501,092).

In contrast, the present application discloses the ability to have Mn:ZnS nanocrystals indiscriminately bind to any surface, hence allowing the general morphological examination of biological specimen. None of the foregoing references disclose or suggest general staining or the use of electroluminescence in imaging or detection.

Commonly-assigned U.S. Pat. No. 10,241,111 discloses the use of electroluminescent nanoparticle labels as reporters in binding assays such as immunoassays and nucleic acid hybridization assays. The disclosed assays detect the presence of analyte compounds in liquid samples by solid phase-immobilized binding partners.

SUMMARY

This section provides a general summary of the disclosure, and is not a comprehensive disclosure of its full scope or all of its features.

The present disclosure provides methods for visualizing biological specimens using EL materials as markers. In some embodiments, there is provided an EL biological specimen visualization method, comprising:

a method for characterizing a biological specimen comprising:

a. applying a biological specimen to a dielectric layer;

b. preparing an electroluminescent assembly comprising a biological specimen in contact with the dielectric layer, a quantity of an electroluminescent material, and a substrate;

c. positioning the electroluminescent assembly between a pair of electrodes;

d. transmitting an electrical signal from a power source through the pair of electrodes to the electroluminescent assembly thereby producing electrolum inescence;

e. capturing the electroluminescence;

f. determining characteristics of the biological specimen in response to the electroluminescence; and g. relating properties of the electroluminescence to the characteristics of the biological specimen.

In some embodiments, the biological specimen can be a tissue section or collection of cells and the electroluminescence produced in the method is captured through the use of a microscope. Electroluminescence light so produced can be detected by any suitable means, including visually, with a consumer digital camera, a CCD camera, or other digital imaging system. The present methods are also applicable to other modes of image capture including fiber optic-type devices. Such methods and devices may find uses for in vivo applications such as endoscopic examinations.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
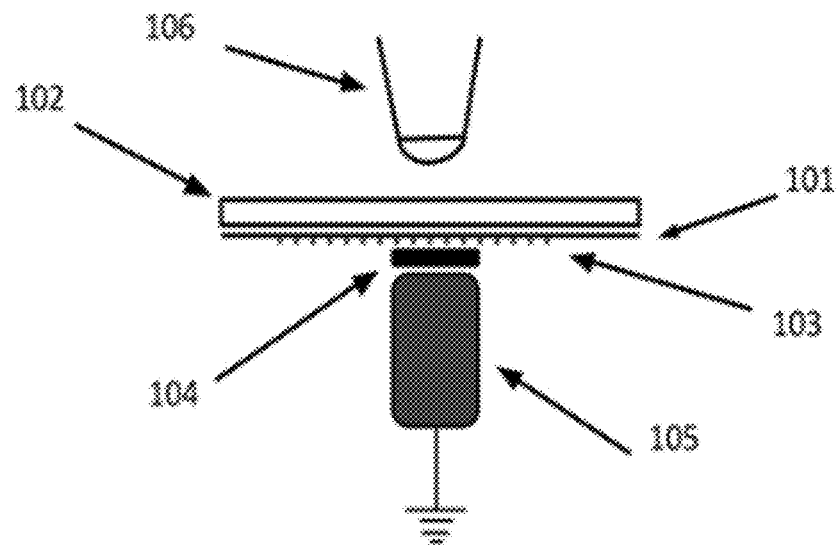
FIG. 1 is a schematic diagram describing an example embodiment of a system for electroluminescence characterization of a biological specimen where an electroluminescent assembly is prepared by placing the specimen with EL material on a transparent conductive substrate.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

According to the principles of the present teachings, methods and devices are described that enable the characterization of biological specimens by the application of electroluminescent materials. When placed in close proximity, including but not limited to direct contact, to a biological specimen, an electrical signal is transmitted, and electroluminescence is generated in response to the presence of the specimen. The electroluminescence thereby produced can be in the form of an image of the specimen. The image is captured by an optical device which collects light and displays or otherwise processes the image according to the particular need or purpose. In general, the method requires preparing an electroluminescent assembly including the sample material (biological specimen), a dielectric layer and a substrate, put together in any order. The method uses an electrical signal, either constant or time-varying such as alternating current, transmitted to the assembly. The device may be configured in a closed-circuit electrical configuration in some embodiments, or it may be in a configuration where the EL assembly is at open circuit with respect to the power source. In the latter configuration, a single terminal from a high-voltage power supply is fed into electroluminescent assembly and can excite the assembly to emit light.

Accordingly, there is provided herein a method for characterizing a biological specimen comprising:
applying a biological specimen to a dielectric layer;
preparing an electroluminescent assembly comprising:
a biological specimen in contact with the dielectric layer,
a quantity of an electroluminescent material, and
a substrate to create the assembly;
positioning the electroluminescent assembly between a pair of electrodes;
transmitting an electrical signal from a power source by means of the pair of electrodes through the electroluminescent assembly, wherein the transmission of the electrical signal through the assembly causes electroluminescence to be produced;
capturing the electroluminescence, wherein the presence and characteristics of the tissue determine one or more electroluminescence properties; and
relating the properties of the electroluminescence to at least one characteristic of the biological specimen.

As described above, the electroluminescence produced in the present methods can be captured through the use of a microscope. The present methods are also applicable to other modes of image capture including fiber optic-type devices. Such methods and devices may find uses for in vivo applications such as endoscopic examinations. The presence of the tissue causes an electroluminescent image to be produced in a pattern that reflects a property of the tissue when a time-varying electrical signal is transmitted by the electrode to all the components In embodiments of the disclosure performed by the use of a microscope, the objective lens system magnifies the electroluminescent signal image for presentation to a viewer or for capture and collection and other optional processing by a camera, sensor or other imaging system. Uses of the methods in the present disclosure in a microscope format permit a form of image investigation and analysis that provides information about the 2D morphology of cells and tissues or, in some applications, about the depth of various components, hence enabling 3D topological characterization of tissue specimens. It should be noted that the present methods permit microscopic investigation of specimens without the use of any external light source since the EL material serves to illuminate the sample in place. However, additional excitation mechanisms, such as a source of electromagnetic radiation, can be coupled with the electroluminescent methods discussed herein to provide a multitude of information regarding the characteristics and radiative properties of the biological specimen under investigation.

The present electroluminescent methods and devices find application also in affinity techniques including immunoaffinity (immunohistochemistry, IHC) and nucleic acid binding-based methods for specific visualization and detection techniques in fixed biological specimens. Suitable EL particles are irreversibly associated with by e.g. passive coating or chemical conjugation to specific binding materials such as antibodies, antigens, streptavidin, DNA segments, RNA segments, or cell surface receptors and the particle conjugate applied to the test biological specimen to permit recognition and affinity binding. After applying electrical excitation as generally described herein, EL emission produced is detected and optionally imaged. Some embodiments, of the present disclosure can employ tagged particles to allow selective targeted imaging via affinity binding interactions as are known in the art. Additionally, the present methods feature the ability for multiplex visualization or detection by using two or more different targeting species each conjugated to an EL material. In these embodiments, the EL material may all be of the same type or may differ in order to produce different color emission or be selectively excited under different electrical conditions, including at pre-determined input voltages, or to differentiate them via optical filtering.

Other advantages of the present methods disclosed herein are readily apparent. When compared to conventional fluorescent microscopy where the exciting source of energy is light, the present methods use electrical energy to excite the emitter, thereby eliminating potential interfering signal (noise) from the system. Fluorescent microscopes used for nanoparticle detection require several optical elements between the detector, e.g. CCD camera, and fluorophore particles. These include high numerical aperture objective lens, angulating light beam coverslip, dichroic mirror, exciting filter, emitting filter and various mirrors to direct the light beam to the detector. Since each of the optical elements causes some light loss, sensitivity is inevitably reduced. In the present EL-based methods, most of these elements can be eliminated. The methods therefore can be simpler and greatly more affordable than fluorescent microscope-based techniques, especially for point-of-care (POC) applications.

Two or more types of particles can be used together in the practice of a method, either simultaneously or sequentially, to produce multiple colors of emission. The different colors of light can thereby signal, e.g., different structural features of the specimen, different regions, or different sub-cellular components. Moreover, multi-colored EL imaging can be prepared with a simple light microscope that is readily available in many medical and research laboratories.

Another embodiment enables a user to perform imaging at different sample depths within a sample without resorting to highly expensive confocal microscopes. Using a simple light microscope or, if desired, a fluorescence microscope, the present methods permit the interrogation of a specimen's 3D-type tissue morphology. Such methods can be performed with only one type of staining particle or with two or more different types, each emitting a distinct color of light. The staining particles located at different heights may experience different electrical power, therefore resulting in emissions at different input electrical powers. Similarly, staining particles of different emission colors can be excited at different input electrical powers. The emission color ratio can further provide information regarding depth and/or the distribution of particles within the sample. In one embodiment, the distance between two emitting sites can be studied wherein the two emitting sites are in the same geometric plane or vertically stacked across different planes. In some embodiments, the distance between two emitting sites can be examined as a function of time to investigate temporal evolution and dynamics, as discussed by Niekamp et al. (2019; *PNAS*).

As mentioned above, complex fluorescent microscope systems are not required to perform EL imaging of specimens in accordance with the presently disclosed methods. Nevertheless, these methods provide the flexibility to couple with photoluminescent (PL) methods and view EL, PL or both EL and PL.

It is anticipated that the present methods can also find applicability in high-resolution techniques previously performed only by fluorescence microscopy. Numerous fluorescence-based high-resolution imaging techniques have been developed in recent years in order to improve spatial resolution beyond the Abbe diffraction limit. These include such techniques as Photoactivated localization microscopy (PALM), Stochastic Optical Reconstruction Microscopy (STORM), Single-Molecule High-Resolution Imaging with Photobleaching (SHRImP), single-molecule high-resolution colocalization (SHREC), and Fluorescence Imaging with One Nanometer Accuracy (FIONA).

Definitions

Electroluminescent (EL) materials and particles. In one embodiment, the electroluminescent material comprises nanoparticles having dimensions less than 100 nanometers. In other embodiments, the luminescent matter may be core-shell particles, flakes, or films having characteristic dimensions less than 100 micrometers. EL materials used in the present disclosure are phosphor materials, which can be selected from semiconductor particles, doped semiconductor particles, elemental Si particles, elemental Ge particles, quantum dots, fluorescent monomers, fluorescent oligomers, fluorescent polymers, phosphorescent monomers, phosphorescent oligomers, phosphorescent polymers, and mixtures thereof.

The solid-state luminescent materials may be chosen from elemental or composite semiconductor materials. For example, elemental semiconductors may be silicon and/or germanium particles. In another example, compound semiconductors may be chosen from group IIB-VI element compositions, such as ZnO, ZnS, ZnSe, CdS, CdSe, CdTe. Composite structures such as particles having a CdSe core with ZnS shell are also contemplated by this disclosure. In yet another example, compound solid-state luminescent materials may be chosen from group III-V elements like GaAs, as well as group IV-VI elements like PbS. The present disclosure also contemplates the use of gold nanoparticles due to their known ability to produce (thermal) radiation in the red-NIR-IR regions of the spectrum under electrical stimulation.

In some embodiments, the luminescent materials may be doped to produce light emission having different colors or wavelengths. In general, transition metal elements as well as rare earth elements are useful as dopants. For example, ZnS particles doped with manganese (Mn) emit orange light; whereas, ZnS particles doped with copper (Cu) produce green light. In other examples, luminescent materials can be doped with samarium (Sm), thulium (Tm), erbium (Er), neodymium (Nd), europium (Eu) or other lanthanide rare earth elements. From these examples, one skilled in the art will recognize other types of dopants may be suitable as well.

Nanoparticles may take many different forms. For example, the nanoparticle may be comprised of one or more of a metal chalcogenide, a group IIB-VI semiconductor compound or a group III-V semiconductor compound. The nanoparticles may be doped, for example with dopants chosen from transition metals or rare earth metals. It is understood that the nanoparticles may include two or more different types of luminescent materials.

In still other embodiments, the electroluminescent material may be an organic fluorescent or phosphorescent material that can be induced to emit light under the application of an electric signal. Such materials can be monomeric or polymeric materials. In some embodiments, the EL material will comprise a continuous layer of an organic luminescent material. A large number and variety of such compounds are known in the literature and used at present, e.g. in producing thin film devices. Listings of such materials are found in many standard treatises on the subject. Commonly used OLED materials include polymeric materials such as poly-phenylene (PPP), polyphenylene vinylene (PPV), polyfluorene, polyaniline, polythiophene (PT), and polyethylenedi-oxythiophene (PDOT), and small molecules such as Alq, metal phthalocyanines, and iridium or ruthenium organo-metallic complexes. The use of any such material is considered within the scope of the present methods. Devices containing two or more layers with different organic luminescent material in each layer are specifically considered to be usable in the methods of the present disclosure, particularly when more than one color of light is to be produced.

In Situ Synthesis Conditions and Procedure

Electroluminescent semiconductor nanoparticles, such as ZnS and transition metal doped ZnS can be prepared by art-known hydrothermal synthesis procedures. Such procedures have produced particles having an average diameter of 35-40 nm. Particles in this size domain provide useful spatial resolution and EL intensities when used in the methods of the present disclosure for general staining and immunohistochemical analyses.

Applicants have devised a novel alternative method for preparing and using electroluminescent semiconductor nanoparticles in situ. In the present disclosure, in situ indicates that the particles are synthesized de novo by applying the chemical precursors to the biological specimen that forms part of the detection assembly and causing the reaction to take place on or in the specimen. Electron microscopic images demonstrated that the particles form a coating over the biological specimen. Use of specimens coated by in situ synthesized EL nanoparticles, when subject to an electrical signal to elicit EL emission, makes sub-μm features visible.

Thus, there is provided herein a method for characterizing a biological specimen comprising:
    applying a biological specimen to a dielectric layer;
    preparing an electroluminescent assembly comprising:
    a biological specimen in contact with the dielectric layer,
    a quantity of an electroluminescent material, and
    a substrate to create the assembly
    wherein the electroluminescent material is synthesized in the presence of the biological specimen;
    positioning the electroluminescent assembly between a pair of electrodes;
    transmitting an electrical signal from a power source by means of the pair of electrodes through the electroluminescent assembly, wherein the transmission of the electrical signal through the assembly causes electroluminescence to be produced;
    capturing the electroluminescence, wherein the presence and characteristics of the tissue to determine one or more electroluminescence properties; and
    relating the properties of the electroluminescence to at least one characteristic of the biological specimen.

In a representative embodiment, in situ-synthesized ZnS nanoparticles can be produced on a tissue coated-ITO glass slide by submerging the slide for a first time period in a solution of a Zn salt (100 mM) optionally containing a transition metal salt, then briefly washing with a wash solution such as PBS, followed by drying at RT. Afterward, the tissue ITO-glass slide surface was covered by solution of a sulfur compound such as $Na_2S$ for a second time period, washed with PBS and dried.

A wide variety of zinc ion source such as zinc chloride, zinc sulfate, or zinc acetate in different concentrations can be used. Also, many sulfide salts can be used such as $Na_2S$, CaS, CaS. $xH_2O$, NaSH or $(NH_4)_2S$. When a transition metal dopant is used it is typically used at 1-10 mol % relative to Zn ion. Solutions are preferably formed in water. Incubation times can be between 5 min to several hours for penetrating Zn ion into the depth of sample and physically bond to sample compartments. Long incubations can be performed with the samples maintained in a humid chamber to prevent drying out the zinc solution. For the sulfide formation reaction part, the incubation time can be considered to be two intervals, before washing and after washing the sulfide source. The reaction between zinc ion and sulfide source is very fast, and can be between 1 min to 1 hour. After the first reaction incubation, the samples are typically washed with water or PBS. After washing, the sample can be used for EL-imaging, but, as our observations suggest, an overnight aging time for the semi-conductive material enhances the light intensity coming out of the in-situ synthesized material in both excitation methods, electroluminescent and photoluminescent.

Biological Specimen

As used in the present disclosure, biological specimen includes cells and tissues and can be alive or dead, fixed or fresh. They can be native, wild, primary samples or lines, cell lines, manipulated, engineered, or immortalized samples. Biological specimens can be cultured in-vitro or obtained in-vivo. Biological specimen also can comprise a part of a cell like the nucleus or mitochondria or be a product of a cell like macromolecules such as nucleic acids, antigenic proteins and receptors. Also biological specimen can be viruses, capsid and similar biological materials. Particular representative examples materials include prokaryotic cells including bacteria and Archea and all their subdivisions, eukaryotic cells including animal cells, plant cells and fungal cells and all the subdivisions, eukaryotic tissues, including multicellular organs or their internal organoids harvested or isolated from plants or animals.

Biological specimens used in the presently described methods can be of the conventional fixed and/or preserved specimens types conventionally used in pathological examinations. Paraffin-embedded tissues, formaldehyde-fixed tissues, fresh frozen or cryopreserved specimens as are generally known in the art are all suitable for the present methods. In addition, fresh, untreated tissue sections can be used directly, thus greatly simplifying the method, while reducing preparation time and cost of materials.

Biological Specimen Characteristics

In various embodiments according to the present disclosure, various characteristics of a specimen can be identified by the present methods can be categorized in the following:
    specific element identification through affinity-related labeling and staining—using an electroluminescent material specifically attached to a binding partner for a target affinity binding substance can provide an indication of their presence/absence, amount or spatial distribution. When the binding partner is an antibody or cognate binding partner to an antibody, the method constitutes electroluminescent Immunohistochem istry (IHC) or immunocytochem istry. Alternatively, the affinity can be a selective staining where electroluminescent material has a specific tendency to adhere to a certain component. The tendency can be innate for an electroluminescent material or be engineered on the surface of the material. For example, through conjugating a reactive group such as a primary amine over the surface of electroluminescent particles, the materials have an affinity toward nucleic acid, which can lead to staining nuclei of cells. Stains for subcellular components including peroxisomes or other organelles are also enabled by the present methods.

Non-specific techniques, which rely on the surface attraction or association of nanoparticles, where nanoparticles are electroluminescent materials. Using this property of the electroluminescent nanoparticle, a thin layer of the nanomaterials can evenly coat the surface of biological specimens. This provides a way to visualize morphology of biological samples and reveal features such as cell margins, shape, and intercellular spaces.

Another advantage of the presently disclosed methods whereby covering the surface of biological sample the 3-dimensional topology of the specimen is determined. Having the nanoparticles on the surface of specimen at different distances from electrodes or at different locations within the EL assembly enables topographic imaging of outer layer of biological specimens.

By manipulating the electrical field experienced by the specimen, other physical properties of selected locations can be assessed. Systematically varying the electrical signal (voltage and/or frequency), the dielectric layer composition or thickness, or pressure applied to the assembly will result in a variation in electroluminescent excitation power that results in variation in light intensity that could be related to the local electrical field intensity, local dielectric constant, local density, and local volumetric dimensions all in nanometer scale.

Dielectric Material

Materials useful as dielectric materials in the present methods include, without limitation, $BaTiO_3$, $SrTiO_3$, barium strontium titanate, calcium copper titanate, nitrile rubber, vinyl glove material, paraffin, polymers including polyethylene, polyimide, poly(dimethylsiloxane), polystyrene, poly(methyl methacrylate), polypropylene, polyethylene terephthalate, polyurethanes, nylon polymers, acrylonitrile-butadiene rubber, vinyl rubber, glass, and graphene. Mixed dielectric materials are contemplated for use as well as using more than one discrete dielectric material in combination. In embodiments where the dielectric material forms a layer between the electroluminescent material and the optical detection device, it may be desirable for the dielectric material to be optically transparent.

Substrate

In embodiments of the present disclosure, a substrate material is generally used for holding the biological specimen in place. The substrate is a rigid material in many embodiments, such as a solid, flat planar surface. Slides and cover-slips of the type commonly used in microscopy techniques can be used. In certain embodiments, it is desirable that the substrate be optically transparent. These can be made of plastic or glass as is generally known and includes conductive glass such as ITO. In some embodiments, the substrate can be opaque when the optical device is accumulating emitted photons directly from the specimen surface. In some embodiments, the light produced may be reflected by the substrate to the optical device without passing through the substrate. In some embodiments, the substrate can serve as one of the electrodes or can hold the electrode in place.

The substrate can work also as a dielectric in the EL-assembly. In addition to the material types listed above, all the dielectric materials mentioned in the previous section could be used as substrate. The substrate also can be a liquid, which carries biological samples labeled with EL material. In another application, the substrate can be liquid carrier of biological sample without EL material on the sample. Mineral oil, castor oil, mineral oil containing barium titanate, castor oil containing barium titanate are some examples for liquid substrate.

Arrangement of Elements of the EL Assembly

The methods and devices of the present disclosure involve the creation and use of an electroluminescent assembly comprising a substrate and a biological specimen in contact with a dielectric material. The order of arrangement of these components may vary according to the method used.

In one configuration depicted in FIG. 1, the biological specimen may be applied to a surface of a substrate and an EL material applied to the specimen or synthesized on the specimen. A dielectric layer is then placed over the specimen.

Figure 2:
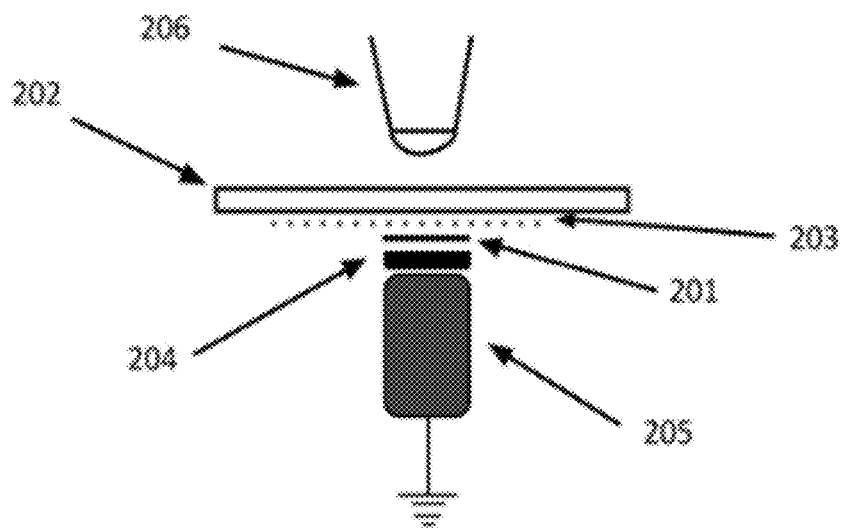
FIG. 2 is a schematic diagram describing an example embodiment of a system for electroluminescence characterization of a biological specimen where an electroluminescent assembly is prepared by coating the EL material onto a surface of a substrate and the biological specimen is applied over the EL material.

In another configuration depicted in FIG. 2, the EL material may be coated onto a surface of a substrate and the biological specimen is applied over the EL material. In this embodiment, the dielectric layer may be placed either over the specimen or in between the specimen and EL material coated-substrate. In some embodiments, two layers of EL material are used, one on the substrate directly and a second on a surface of the biological specimen not in contact with the substrate.

In some embodiments, the assembly can serve as one of the electrodes (i.e. the specimen or the substrate or the dielectric)

To excite the nanoparticles according to the previous examples in order to determine at least one characteristic of a tissue specimen, the tissue on ITO glass slide is stained through one of the procedures in the examples described below and mounted on one of the electrodes which has been covered by a dielectric layer. The other electrode of a power source is connected to the ITO surface of an ITO glass slide. The whole setup is designated an electroluminescent assembly and is depicted in FIG. 1.

Figure 3:
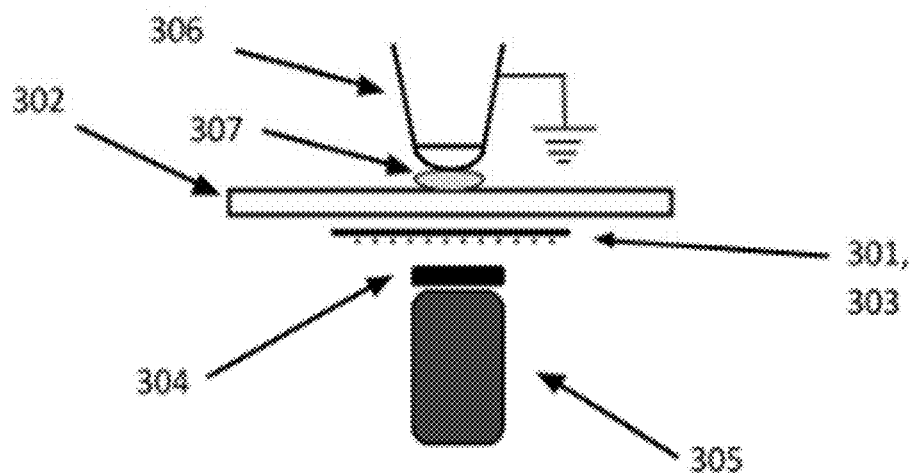
FIG. 3 is a schematic diagram describing an example embodiment of a system for electroluminescence characterization of a biological specimen where an electroluminescent assembly is prepared and a liquid droplet works to electrically couple the EL assembly to a microscope body.

In another embodiment of the disclosure shown in FIG. 3 the EL-assembly can be mounted on an electrode and the EL-assembly with the electrode is situated on an upright white light microscope 306 and the electrode is connected to the energizing electrode of a power source. A liquid droplet 307 then is placed between the coverslip on which a tissue slice 301 is mounted and stained, and microscope lens. With this setup, the droplet works to electrically couple the EL assembly to the microscope body. Moreover, through using the conductive droplet, ITO-coverslip is replaced by simple coverslip 302 which means in this configuration there is no need to use ITO coated slides to energize nanoparticles. The glass slide on which tissue slice is mounted needs only to be thin enough to pass the electrical field to nanoparticles 303.

In an alternative embodiment, order to visualize tissue compartments without staining them, the method of example 5 was performed using an assembly depicted in FIG. 2. A 5 μm thickness cardiac tissue section 201 was mounted on an ITO-glass slide 202 which had been coated with Mn-doped ZnS nanoparticles 203 using EDC-NHS chemistry discussed in example 5. Then the tissue with its substrate which is the coated ITO-glass slide was attached on the tip of electrode 205 which had been covered by a thin layer of nitrile butyl rubber as the dielectric 204. The EL-assembly with the second electrode was installed on the stage of light microscope 206 and the ITO-glass slide was connected to the power source through a copper tape attached to the ITO surface. The capturing process was followed as described in example 7.

In another embodiment of the disclosure, the arrangement of the EL-assembly can be changed in a way that electroluminescent materials are not in direct contact with the biological specimen. To set the configuration of EL-assembly, it is started by coating the ITO-surface of an ITO-glass slide, the substrate, with electroluminescent material. The electroluminescent materials on the ITO surface, then, is covered by a dielectric layer. At the next step, a biological specimen which is already in contact with ground electrode is come to contact with the dielectric layer to complete the EL-assembly. On the other side of the EL-assembly the ITO-surface is attached to energizing electrode of power source via a copper tape.

Although the electroluminescent materials may not, in some embodiments, be in direct contact with the biological specimen, the biological specimen has a significant effect on electromagnetic field passing through it toward the electroluminescent material on the other side of the dielectric layer. By adjusting the dielectric layer and electromagnetic field properties, the effect of the biological specimen is significant enough to induce the electroluminescent materials in different intensities to produce a signal image which resembles at least one characteristic of the biological specimen.

Electrodes

In the methods of the present disclosure, a set of electrodes is used between which the EL assembly is placed. The electrodes can be of various compositions, including but not limited to copper, steel, gold, zinc, and silver. The electrodes can be at-least partially transparent, such as Indium Tin oxide (ITO)-coated glass, metal-sputtered polymer. In some embodiments, at least one of the electrodes is in a liquid form, such as salt water solution, liquid elemental Mercury, and molten tin and lead or their alloys. In other embodiments, the electrode is a gel, such as electrolyte gel. In some embodiments, the electrode is disposable. In some embodiments, the electrode may be consumed. In another embodiment, the electrode may be encased at least partially inside a dielectric material.

The physical properties of the electrodes can be changed in order to manipulate the electric field across the EL assembly. In one embodiment, the surface area of the electrode is reduced to limit the region of excited stained tissue in order to preserve the parts of the tissue located outside the operational scope of the microscope objective. In another embodiment, the electrode has a spherical surface to avoid arcing across the electrodes at high operational voltages. In yet another embodiment, the electrode is designed flat for uniform electric field for three-dimensional measurements. In yet another embodiment, the thickness of the electrode is reduced. In other embodiments, water droplet is used to provide a flat surface against the region of interest to provide uniform electric field. In other embodiments, the cross section of a pin-electrode is reduced for increased field density at a small region of interest. In some embodiments, the El assembly is coated via metal sputtering wherein the metal will serve as temporary or permanent electrodes.

Electric Signal

In the methods of the present disclosure, the electrical signal transmitted to the EL material in the assembly should be supplied at a potential sufficient to excite the EL material to an electronic excited state in order to produce light emission. Sufficient potential can readily be determined empirically or by consulting reference materials. The methods are not limited to any particular waveform, frequency, or phase angle. And can be applied for any convenient length of time to produce EL emission sufficient for detection and imaging. In some embodiments, the electrical signal can be in the form of a constant, direct-current type of signal. The signal should be supplied to the system at a voltage suitable to elicit electroluminescence from the electroluminescent material. Typical AC operating voltages are in the range of 110 to 5000 volts.

In a representative embodiment characteristic of the use of so-called OLED materials, a Ru complex was applied and energized according to the present methods at 12 V DC.

In some embodiments, the electrical signal can take the form of a time-varying electrical signal. As used in the present disclosure this type of electrical signal includes modulating electrical signals such as an alternating current having a sinusoidal waveform of a wide range of frequencies. Frequencies useful in the practice of the present methods can range from 1 Hz to 200 kHz, or in some embodiments, including in Mn-doped ZnS nanoparticle assemblies, from 20-50 kHz. Other forms of modulated amplitude signal that provide a change with respect to time, such as square waves, sawtooth waves and one or more pulsed electrical signals, are considered to be within the scope of the disclosure.

It is envisioned that, in embodiments of the present methods where more than one electroluminescent material is used, it may be advantageous or sometimes necessary to alter or otherwise sequentially supply different electrical signals, e.g. different voltages. In this way, the optimum electrical signal can be selected for each material. In some embodiments, it will enable selectively turning on electroluminescence from one of the electroluminescent materials. Such a method is useful in distinguishing different species within a specimen.

In one embodiment, there is provided an EL biological specimen visualization method, comprising:

Attaching electroluminescent material to a biological specimen;

Mounting the biological specimen with the attached electroluminescent material on an electroluminescent platform, the electroluminescent platform comprising a first electrode disposed in a support member;

Transmitting an alternating current electrical signal having a frequency of 30 kHz at a potential of 1200 V AC from a power supply to the first electrode of the electroluminescent platform Providing a second electrode to allow the transmission of the electrical signal through the biological specimen with the attached electroluminescent material, wherein the transmission of the electrical signal causes at least a fraction of the electroluminescent material to luminesce; and Capturing the luminescence Power Source The power source in embodiments of the present disclosure where a constant electrical signal is supplied can be any ordinary source of DC power including batteries and DC power supplies. Power sources used to produce a constant electrical signal in the present methods should be capable of generating few to hundreds of watts of electric power. The constant voltage range on such power supplies can supply 1-500 VDC. Power supplies generating time-varying signals can operate within 1 V-10 kV at frequencies ranging between 1 Hz-10 MHz. The time varying signal may have simple waveforms such as a square wave configuration or a complex form. The signal can be changed with time. Multiple power supplies can be coupled to generate a complex waveform.

The power source in some embodiments, where it is desired to supply a time-varying electric signal can be a cold cathode fluorescent lamp (CCFL) inverter. CCFL inverter operates at high voltage (few volts to tens of kilovolts) and high frequency (10-50 kHz). CCFL are often used for backlighting liquid crystal display (LCD) panels. The CCFL models include for example: JKL components (BXA-24529, BXA-601), TDK (CXA-M10M-06Y15R, CXA-P1612-VJL, CXA-L0505-NJL), etc. CCFL circuits normally operate at an input voltage of 0-24 VDC. The voltage output of CCFL can be adjusted with modifying the inverter circuit elements and/or changing the input voltage. The latter was accomplished with the use of batteries, AC/DC transformer (adapters), and/or a lab-grade variable direct current (DC) power supply. In particular, VOLTEQ HY3006D is a regulated linear DC power supply and is continuously adjustable at 0-30 VDC and 0-6 A. Plug & play systems are also within the scope of the present disclosure. In this case, the power supply is the typical North American/European power outlet with single-phase unit which has a 0-110/220VAC output voltage and frequency of 50/60 Hz. Other commercial wave generators can also be used. For instance, the SIGLENT SDG805 5 MHz 125 MSa/s Arbitrary Waveform Generator was used to generate time-varying electrical signal of various waveforms, including sine, square, ramp, pulse, and arbitrary/custom waveforms. The wave generator was further used to generate voltage and frequency sweeps ranging $|V_{PP}|<20$ volts and $f<5$ MHz, where $V_{PP}$ and f represent the peak-to-peak voltage and wave frequency, respectively.

Electroluminescence Properties

The electroluminescent devices of the present disclosure generate light at wavelengths, more accurately ranges of wavelengths, governed by the emissive properties of the phosphor materials used. In general, light is produced in a region of the electromagnetic spectrum spanning the ultraviolet, visible near infrared and infrared wavelengths. One or more colors of light can be generated in the methods of the present disclosure by deliberate choice of phosphors.

In various embodiments described below, additional properties of the emitted electroluminescence may be of special significance. The intensity of light being produced may indicate the relative amount of EL material present. The spatial distribution of light can provide information about the 2D morphology or 3D topology of the specimen being examined. In embodiments where EL material is supplied in the form of particles conjugated to affinity substances, light patterns showing the shape or presence of substructures may result. Combining spatial and color information from multiplexed detection formats permits the acquisition of additional types of information from test biological specimens.

Capturing Electroluminescent Signal

Electroluminescent light produced in the present methods may be detected by any suitable means and is not limited to any particular mode of detection or visualization. Light produced in the visible portion of the spectrum can be detected by eye, for example. Other means of detecting the emitted light include digital cameras, photographic film, CCD chips, and sensor arrays. Commercial or purpose-built luminometers also can be used to detect and measure the electroluminescence produced in the present methods.

Luminometers having a measurement chamber designed to house a single sample tube such as a Turner Designs TD 20/20 or similar can be used. Alternatively, luminometers designed to receive a 96-well microplate and measure each of the wells can also be used. In some embodiments, it may be desirable to select a portion of the wavelengths of light emitted. In such cases the method may further comprise the use of monochromators (prism or grating), or optical filters including low-pass, high-pass and notch or band-pass filters.

Optical devices including microscopes using a variety of lenses for optical magnification and selecting a plane of focus can be used in some embodiments, to transmit light to appropriate recording and/or measuring devices. Cameras, including film and solid-state digital camera consumer cameras as well as CCD chip-based cameras of the type used in astrophotography, can all be used within the methods of the present disclosure to record EL signals and images. Data acquisition systems for permanent storage, retrieval and data manipulation and analysis can be used for documentation and storage of data in conjunction with the methods of the present disclosure.

Optical Devices

The electroluminescence produce can be in the form of an image of the specimen. The image can be a two-dimensional image or, in some applications, a three-dimensional image as described further below. In these embodiments, the electroluminescence produced by the methods and devices of the present disclosure will be collected by means of an optical device comprising optical elements such as lenses. An exemplary system of optical elements is a light microscope. A simple light microscope with one or more different interchangeable lenses can be used to provide different degrees of magnification of sample image. In embodiments involving the dual electroluminescent/photoluminescent investigation of biological specimens taught herein, the optical device used can be a conventional fluorescence microscope. While more complex and costly instrumentation are not required, they may nonetheless be employed in conjunction with the present electroluminescent methods, especially in pursuit of more sophisticated imaging techniques referred to above in the present disclosure.

Relating the properties of the electroluminescence to at least one characteristic of the biological specimen Once captured by an optical device and, optionally, stored and additionally processed, the light signal(s) or image is identified with, correlated or quantified with one or more features, components or contents of the biological specimen. This step or process can consist of identifying or evaluating the 2D features of a specimen such as locating cell boundaries or identifying different cell types. In some embodiments, it can consist of assessing the 3D topology of a specimen or evaluating thickness in different regions, or looking at the course of features in the z-direction. In embodiments using EL material or EL nanoparticle-binding partner conjugate, e.g. antibodies and the like, the relating step can consist of determining the location, distribution or number of target substances based on the pattern and EL intensity in areas showing signal in a specimen. When more than one label is used, relative or differential information can be obtained.

Applications and Uses

General Staining Used for Surface Imaging

As discussed above, the methods and devices of the present disclosure find application in providing a process for general staining of cellular material. By either applying a pre-made electroluminescent material, such as nanoparticles, or synthesizing an electroluminescent material in place, applying an electrical signal to the assembly will produce images showing structural features, e.g. different cell types, of the specimen.

In one embodiment, there is provided a method for imaging a biological specimen comprising:
applying a biological specimen to a dielectric layer;
preparing an electroluminescent assembly comprising:
a biological specimen in contact with the dielectric layer,
a quantity of an electroluminescent material, and
a substrate to create the assembly;
positioning the electroluminescent assembly between a pair of electrodes;
transmitting an electrical signal from a power source by means of the pair of electrodes through the electroluminescent assembly, wherein the transmission of the electrical signal through the assembly causes electroluminescence to be produced; and
capturing the electroluminescence through a microscope, wherein the presence of the electroluminescent material creates an image of the biological specimen.

In a representative embodiment of the setup, by providing a ready-to-use EL-assembly consisting of a coated ITO-glass slide with electroluminescent material covered with dielectric layer, just through putting a slice of a fresh unstained tissue specimen on the EL-assembly; a rapid live image of cells within the tissue and their exposed compartment is produced. The speed and simplicity of this system provides rapid results with minimal operator intervention.

General Staining Used for Topology Imaging

Another embodiment of the disclosure can reveal $3^{rd}$ dimension data from a biological specimen. Without wishing to be bound by any particular theory of operation, there appears to be a certain distance between the dielectric layer outermost surface and electroluminescent materials which is the most effective distance for exciting the electroluminescent materials. As a result, electroluminescent materials are excited in a distance-dependent manner from dielectric layer through the electromagnetic field generated by the applied electrical signal located. The resulting images can thus provide an indication of the three dimensional topology of a specimen.

Moreover, using this property by changing the distance between biological specimen and the dielectric layer, different levels of biological specimen will be positioned for optimal excitation the electroluminescent materials. Serial images can be produced which reveal the characteristics of various depth levels.

Two-Color Method for Three-Dimensional Imaging

A significant new capability of the microscopic imaging methods of the present disclosure is that different levels of a specimen can be visualized without complex procedures, multiple sectioning or expensive confocal microscopy equipment. This is because the electromagnetic field density is in effective range at a distance range from the energizing electrode and the distance depends upon factors including the applied voltage and frequency, the nature or the electroluminescent material and the dielectric layer properties including its dimensions. In one embodiment, by applying different pressure on the substrate on which a biological species is in contact, different levels or strata of biological species can be detected, possibly by mechanically deforming, e.g. squeezing, the dielectric layer to reduce its related dielectric strength.

In an embodiment of this facet of the present methods, through having different color electroluminescent material at different levels on an ITO-glass slide which is covered by a dielectric layer, when the covered ITO-glass which is already connected to a power source comes in contact with a biological specimen, which can be an in-situ detection, wherever the biological specimen shows different mechanical stiffness, different pattern of deformation will shape on dielectric layer that ends to different level excitation of electroluminescent particles which have different color. Using this configuration of the art, the morphology and topography and rigidity of tissue at in-situ, ex-situ, ex-vivo, in-vivo condition is attainable. Some specific exemplary applications of this aspect of the presently disclosed methods include study and diagnostic and prognostic application on cardiovascular stenosis, blood vessel calcification, blood vessel embolism, congestions, edema, hemangioma, atherosclerosis, aneurisms, gastric folds and rougae, intestinal villi, respiratory endoscopy and bronchoscopy, tumor and lump detection in or on a patient's body.

Affinity Staining Used for Immunohistochemistry and Immunocytochemistry

In other embodiments, the methods of the present disclosure can be applied to the detection and analysis of various species within a biological specimen by means of employing EL material-labeled specific binding materials. Such methods constitute electroluminescent immunocytochemical (ICC) and immunohistochemical (IHC) analyses.

A representative IHC procedure can consist of following steps:

A. secondary antibody labeling with EL materials,

B. tissue ITO-glass slide is prepared as described, e.g. as described in example 1, C. primary antibody is incubated on the tissue ITO-glass slide, followed by washing with wash buffer and further washing with PBS, D. unoccupied surface markers on the tissue is blocked by incubating in a BSA solution, then washed with wash buffer followed by PBS, E. incubating the tissue ITO glass slide with labeled secondary antibodies, followed by washing with wash buffer followed by PBS.

Linking a secondary antibody to EL material can be done by using various art-known methods, including, without limitation, MPA-capped, Mn-doped ZnS nanoparticle covalently conjugated to a secondary antibody using EDC-NHS chemistry, BSA-coated nanoparticle covalently conjugated to a secondary antibody using EDC-NHS chemistry, streptavidin conjugate on nanoparticles linked to a biotinylated secondary antibody, Biotinylated BSA coated on nanoparticle is linked to a streptavidin conjugate secondary antibody, and biiotinylated BSA on nanoparticle directly linked to streptavidin conjugated primary antibody.

Multi-Color Immunohistochemistry for Multiplex Analysis

In a further embodiment, a multiplexing technique as described immediately above can be de developed to label different surface markers on a tissue section. As a non-limiting example, through bioconjugation of secondary antibodies from different species to nanoparticles with different emission wavelength and incubating the specimen with primary antibodies from different species that are specifically bindable with the conjugated secondary antibodies, multiplex labeled immunodetection is possible. The use of different color emitting EL nanoparticle labels produces multiple colors in one captured image without using light filters. In fluorescent microscopy, to have a multicolor image made of green and orange lights, the sample has to be excited by blue range excitation light and using blue filter and take an image from the green light emission then the filter has to be changed to green light filter and again the sample is excited by blue-green light to captured the second color image. Subsequent superimposing of the two images on each other constructs a multicolor image. In contrast, the present method applies a single excitation mechanism to excite and generate EL signals of all labels in one step; the method does not need any filters to eliminate excitation wavelengths.

EL Imaging Combined with Photoluminescence

The method of the present disclosure may further comprise generating and detecting photoluminescence in addition to electroluminescence. In some embodiments, the method can further comprise irradiating the biological specimen in the electroluminescent assembly with a light source to produce photoluminescence from the biological specimen and capturing the photoluminescence. In such methods, two sources of information can be acquired. The term photoluminescence contemplates, fluorescence, phosphorescence, delayed fluorescence, energy transfer fluorescence. The form of photoluminescence generated will be determined by the properties of the electroluminescent material chosen for this purpose.

As described above, EL excitation can turn on just the electroluminescent material in a thin layer inside the samples. In another embodiment of the disclosure, an EL-assembly with electrodes and power source can be mounted on a stage of a fluorescent microscope upon which the sample can be excited dually, by electroluminescence and by light to produce photoluminescence (PL), either fluorescence or phosphorescence, depending on the material. Using this novel method of microscopy, typical fluorescent microscopy reveals the presence of the fluorophores in a specimen. At the same time, by applying an electrical signal, the EL-assembly electroluminescent active material also emits. Doing so locates a specific 3D location of electroluminescent material in the image. Thus, two distinct types of information are obtained on the same specimen at the same time. The above embodiment is described referring to using only one type of EL material to generate two different sets of image information. The same technique may also be adapted to using two different EL materials, one being used in EL mode and the other in PL mode. This degree of flexibility permits separately optimizing the choice of EL material for each mode for color, intensity or other parameter.

In another embodiment of the simultaneous use of PL and EL imaging, a non-EL-active fluorescent stain such as Eosin, can be used in conjunction with an EL material. The PL dye is, in effect, used as a counter stain, while the EL-imaging is for a specific staining. In another embodiment, Autofluorescence, i.e. spontaneous fluorescence from unstained specimen, can be elicited from a specimen upon suitable irradiation while EL is also produced from an EL material general stain.

Other Applications and Uses

The above methods can be modified to operate within an organ's cavity. In one embodiment, an endoscopic camera is coupled with an electroluminescent assembly. The electroluminescent assembly comprises electroluminescent nanoparticles disposed over an electrode with a dielectric material that further insulates the particles. Upon contacting the organ's tissue, the electroluminescent assembly generates light, which is captured by the endoscopic camera. In another embodiment, the endoscopic camera is replaced by a fiber optic that collects the generated light from the electroluminescent assembly and feeds a luminometer which measures the change in the electroluminescent assembly's light intensity with time.

Devices and Systems for Performing Electroluminescent Characterization

The present disclosure further provides devices and systems for conducting electroluminescent characterization of biological specimens. Such devices and the systems that contain or use them involve preparing an electroluminescent assembly from a substrate, a biological specimen, an electroluminescent material and a dielectric layer as described above. In one embodiment there is provided a device to characterize an electroluminescent assembly consisting of a biological specimen in contact with a dielectric layer, a quantity of an electroluminescent material, and a substrate, the device comprising:

a power source, a pair of electrodes operably coupled to the power source, wherein at least one electrode of the pair of electrodes is transparent, and an optical device;

wherein an electroluminescent assembly is positioned between the pair of electrodes;

wherein the power source supplies power to the electroluminescent assembly by means of the pair of electrodes;

wherein the power supply causes the electroluminescent assembly to produce electroluminescence;

wherein one or more properties of the electroluminescence are determined by the characteristics of the electroluminescent assembly; and wherein the optical device captures the electroluminescence from the electroluminescent assembly through the at least one transparent electrode of the pair of electrodes.

Example embodiments will now be described more fully with reference to the following examples and accompanying drawings.

Example 1 In-Situ Synthesis of the electroluminescent (EL) Nanoparticles

One type of semiconductor EL nanoparticles which can be applied on biological specimen is the tone that is synthesized on biological specimen which is describe hereinafter.

An indium tin oxide coated glass slide (ITO-glass) was activated to adhere a thin slice of mammalian organ tissue permanently through dipping the ITO-glass in 0.5% (w/v) gelatin solution in DI water which contains 0.05% (w/v) potassium chromium sulfate dodecahydrate for 30 s and dried at room temperature (RT) overnight. The biological specimen which is a mammalian organ thin layer tissue (5 um), a sheep cardiac tissue more specifically, was mounted on activated ITO glass slide via conventional histological sample preparation method for paraffin embedded tissue.

To produce in-situ synthesized nanoparticles, the tissue-ITO glass slide was submerged for 1 h in $ZnCl_2$ solution (100 mM) containing 1% Mn ion, slightly washed with PBS (phosphate buffer saline 0.1 M), and dried at RT. Afterward, the tissue ITO-glass slide surface was covered by $Na_2S$ solution (20 mM) for 10 min, washed with PBS and dried. Mn-doped ZnS semiconductor lattice forms on the different compartments of the cells in the tissue based on relative affinity between them using the tissue as a scaffold.

In this example by using manganese ion as the dopant the electroluminescent emission is in the range yellow-orange wavelength. Through changing the dopant, different color light emission will be achieved. For instance, by using copper ion (0.2%) instead of manganese, green light is emitted. Undoped zinc sulfide emits in the range of blue wavelengths.

Example 2—General Staining

Mn-doped ZnS nanoparticles (ca. 37 nm avg. diameter) containing mercaptopropionic acid (MPA) as capping agent (ca. 1:20 MPA:Zn) were prepared separately according to known procedures and dispersed in DI water (10 mg/mL). The resulting particle suspension was used as a staining agent. Samples were prepared for electroluminescent imaging by the following procedure.

A tissue-ITO glass slide was prepared as described in example 1. The tissue surface was submerged under electroluminescent semiconductor nanoparticles, e.g. Mn-doped ZnS (10 mg/mL), followed by incubation at RT for 5 min and then washing the sample surface with PBS.

Through using different capping agents and different surface charge of the nanoparticle surface, the nanoparticles show different affinity to different cells' compartments in the tissue slide. Through using different dopants and different components of semiconductor nanoparticle, the electroluminescent emission wavelength materials are produced.

Example 3—Immunohistochemistry (IHC)

A representative IHC method consists of the following steps:

a. Secondary antibody labeling with EL materials by one of the listed protocols. In this example embodiment a secondary antibody was linked to MPA-capped Mn-doped ZnS nanoparticles using EDC-NHS chemistry. Other methods described above in this disclosure have also been employed.

The steps for preparation of electroluminescent nanoparticles labeled antibody (NPs-Ab) are described herein. 30 µl of MPA-capped Mn-doped ZnS nanoparticles (50 nm particle size, 10 mg/mL) were suspended in deionized (DI) water (1 mL) to form a suspension. 21 µL of ethyl-3-(3-dimethylaminopropyl)carbodiimide.HCl (EDC, Thermo Scientific, 30 μg/mL in DI water) was added to the suspension and the suspension was mixed for 1 min at RT. After 1 min, 5 μL of NHS (260 μg/mL in DI water) was added to the suspension. The suspension was incubated for 15 min at RT. Then 2 μL of 2ME (1:1000 VN solution in DI water) was added to the suspension to make a reaction mixture. Anti-BSA, rabbit IgG fraction (Invitrogen), 25 μL of 2 mg/mL, was added to the reaction mixture and the reaction mixture was incubated for 2 h at RT. Reaction mixture was centrifuged at 14000 RPM for 10 min and the supernatant was decanted. For the purification step, the precipitates were re-dispersed in PBS and centrifuged again at 14000 RPM for 10 min and the supernatant was decanted. The purification step was repeated 3 times. After the last purification step, the precipitates were dispersed in 1 mL of PBS.

b. Tissue ITO-glass slide is prepared as described in example 1.

c. Primary antibody is incubated on the tissue ITO-glass slide for 1 h at RT, followed by washing with wash buffer made from 0.05% Tween 20 in 0.1M, PBS hereafter is called wash buffer, for 5 min, afterward, 15 min washing with PBS (0.1M).

d. Unoccupied surface markers on the tissue is blocked using BSA (1% w/v) incubated for 1 h at RT, then washed with wash buffer for 5 min and PBS for 10 min e. At this step labeled secondary antibodies which were prepared at step a is incubated on the tissue ITO glass slide for 1 h at RT, followed by washing with wash buffer for 15 min and PBS for another 15 min, f. After the steps samples is ready for EL imaging which is described in the following examples.

Example 4—Immunohistochemistry with Counterstain

In another embodiment, multiplexing without using different optical filters is demonstrated. A cardiac tissue sample was prepared according to the procedure of example 1. After tissue ITO-glass slide preparation, the IHC procedure was performed based on the protocol in example 3. The specimen was then generally stained using the protocol in example 2, except Cu-doped ZnS nanoparticles were applied on the tissue. By applying the sample onto the assembly EL device and applying a 2500 Vp-p signal at 35 kHz, Mn-doped nanoparticles emitted yellow-orange color light which is emitted from sarcomere region of the cardiac cells and Cu-doped nanoparticles emitted green color light which is oriented from the rest of the tissue surface.

Example 5 with Reference to FIG. 2—Unstained Tissue Visualizing

In another exemplary embodiment, cells in a tissue slice are visualized without directly staining the tissue itself. This method is very helpful to reduce the time of histopathological sample preparation at point-of-care where the time of getting the pathology results is crucial for success of treatment.

To show this aspect of the present methods, an ITO glass slide was coated with a thin layer of semiconductor nanoparticles using one of two procedures described below. These two methods for coating the ITO-glass with semiconductive nanomaterials are not intended to limit the processes of coating that may be used.

Covalent coating process—The ITO glass was cleaned with ethanol and air dried. Clean ITO glass was submersed in a solution of (3-aminopropyl) triethoxy silane (99% Aldrich, 2% VN solution in acetone) for 30 s, followed by rinsing the ITO glass with acetone (HPLC grade, Fisher Chemical). The ITO glass was air dried. In the next step the ITO glass was washed with a wash buffer three times and rinsed with PBS. The wash buffer was PBS containing 0.5% VN tween 20. The activated ITO glass slide (hereafter called ITO glass-$NH_2$s) was dried and used for the next steps of the process.

The steps for coating of electroluminescent nanoparticles on the ITO glass-$NH_2$s are described herein. 300 μl of MPA capped Mn doped ZnS nanoparticles (50 nm particle size, 10 mg/mL) were suspended in deionized (DI) water (1 ml) to form a suspension. 21 μL of EDC (300 μg/mL in DI water) was added to the suspension and the suspension was mixed for 1 min at RT. After 1 min, 50 μL of NHS (260 μg/mL in DI water) was added to the suspension. The suspension was incubated for 15 min at RT. Then 2 μL of 2ME (1:100 VN solution in DI water) was added to the suspension to make a reaction mixture. The surface of the ITO glass-$NH_2$s was covered by reaction mixture for 2 h at RT and then washed with wash buffer and DI water each for 5 min.

Adsorptive coating process—The other way of coating the ITO glass slide is based on using surface activity of the nanoparticles. 300 μL of MPA-capped Mn-doped ZnS nanoparticles (50 nm particle size, 10 mg/mL) were suspended in DI water (1 mL). Then the ITO glass slide was covered by the suspension for 1 h and then briefly washed with DI water for 30 s. In this method the particles are noncovalently adsorbed to the surface of ITO glass slide. During different washing steps or rubbing the nanoparticles-ITO surface of the ITO glass slide to a solid surface, loss of the nanoparticles will occur.

After running the aforementioned coating methods, the coated ITO-glass slide was ready for mounting a tissue slice on its coated surface. The tissue slice can alternatively be prepared through, but not limited to, paraffin embedded fixed tissue sectioning using typical microtome, or by frozen sample in liquid nitrogen sectioning using conventional cryo-sectioning methods. After preparing the tissue section, it was mounted on the coated side of coated ITO glass slide. The rest of the sample preparation was similar to typical tissue glass slide preparation for standard histology.

By applying the sample onto the assembly EL device and applying a 2500 Vp-p signal at 35 kHz, Mn-doped nanoparticles emitted yellow-orange color light from interstitial spaces between the cells and the cavities in the cells. Even though there is an even coating of nanoparticles on the surface of ITO glass, the cavities and interstitial spaces between the cells in the tissue slice are the only locations of the cells which emit.

Example 6—Generally Stained Tissue with Background Counter Stain

To have a generally stained tissue with a counter stain at interstitial spaces between the cells and the cavities inside the cells, a tissue on coated ITO glass slide was prepared following the procedure of example 5. Afterward, 300 μL of MPA-capped Cu-doped ZnS nanoparticles (50 nm particle size, 10 mg/mL) were suspended in deionized (DI) water (1 ml). The tissue on the coated ITO glass slide was submerged in the suspension for 1 min and then washed with PBS for 1 min.

By applying the sample onto the assembly EL device and applying a 2500 Vp-p signal at 35 kHz, Mn-doped nanoparticles emit yellow-orange light which is emitted from interstitial spaces between the cells and the cavities in the cells.

Even though there is an even coating of nanoparticles on the surface of ITO glass, the cavities and interstitial spaces between the cells in the tissue slice are the only locations which emit. Cu-doped nanoparticles emit green light which is oriented from the rest of the tissue surface.

Figure 5:
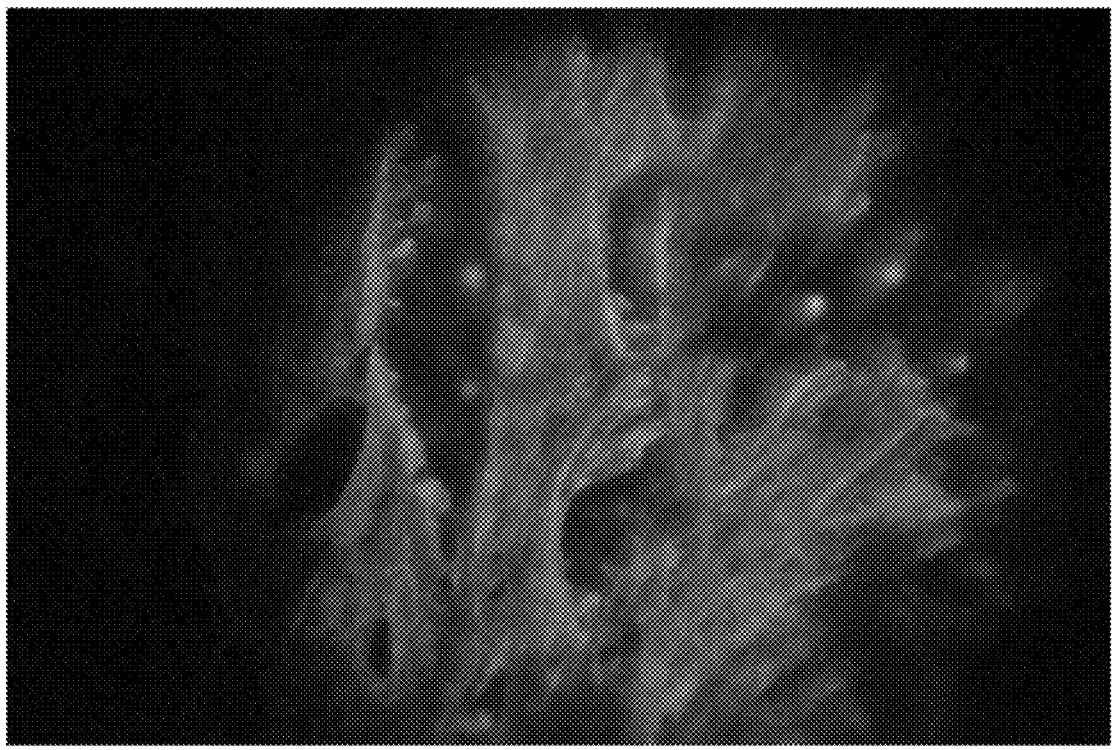
FIG. 5 is a photographic image of a section of cardiac tissue as described in example 7.

Example 7 with Reference to FIGS. 1 and 5—EL Assembly Type 1—Tissue on ITO Glass EL imaging of a generally stained cardiac tissue—Having followed example 2 in which a cardiac tissue on ITO glass slide was prepared and stained for morphology study of cardiac muscle cells, a copper tape was connected to the ITO surface of the ITO glass slide 102. The tissue 101 stained with Mn:ZnS 103 on ITO glass was mounted on a dielectric layer made of a thin layer (<1 mm) of nitrile butyl rubber 104 which was attached to the top face of a metallic cylinder 105. The metallic cylinder diameter was not more than 2 mm in this embodiment. The metallic cylinder was connected to the power source which produced 2500 Vp-p at 35 kHz. The energized wire of the power source was connected to the copper tape 1. The EL assembly sandwiched between the two electrodes was mounted on a light microscope 106 which was equipped with a Canon digital color camera. The EL image was captured for 3 s at magnifications ranging from 10-100×, while simultaneously energizing the EL assembly. FIG. 5 is an image obtained at 10× with a 3.5 s exposure.

Example 8 with Reference to FIG. 1—EL Assembly Type 1—Tissue on Coverslip and Coverslip as the Dielectric Preparing the assembly—Tissue section was attached on a coverslip and prepared for staining. After staining through one of the methods described in examples 1 to 6, the coverslip was mounted on the tip of metallic cylinder as the second electrode 105. In this configuration of the EL assembly, the coverslip worked as the dielectric layer 104 and the substrate to keep the tissue in its original shape. Moreover, in this configuration of the EL-assembly, the stained face of the tissue is towards the microscope lens which lends to higher quality images from outermost layer of tissues. Because the coverslip is the dielectric layer of the EL-assembly, it must be thin enough to allow nanoparticles on the other side of the coverslip to be excited. In this example the coverslip thickness was 160 µm. To capture EL images, the EL-assembly is covered by an ITO-coverslip which was attached to one of the electrodes of the power source. All the EL-assembly plus the electrodes were mounted on a light microscope stage and captured using the method described in example 7.

Figure 6:
FIG. 6 is a photographic image of a section of cardiac tissue as described in example 9.

Example 9 with Reference to FIGS. 2 and 6—EL Assembly Type 2—Unstained Tissue on EL Material Coated ITO Glass In order to visualize tissue compartments, the method of example 5 was performed using the assembly configuration of FIG. 2. A 5 µm thickness cardiac tissue section (201) was mounted on an ITO-glass slide (202) which had been coated with Mn-doped ZnS nanoparticles (203) using EDC-NHS chemistry. Then the tissue with its substrate which is the coated ITO-glass slide was attached on the tip of electrode (205) which had been covered by a thin layer of nitrile butyl rubber as the dielectric (204). The EL-assembly with the second electrode was installed on a light microscope's stage and the ITO-glass slide was connected to the power source through a copper tape attached to the ITO surface. The capturing process was followed as described in example 7. A representative image is shown in FIG. 6.

Example 10—EL Imaging of Immunohistochemically Attached EL Material on ITO-Glass Through following steps a-f of the procedure described in the example 3 a cardiac tissue sample, on which α-Actinin sarcomeric proteins were labeled by Mn-doped ZnS nanoparticles, was prepared on the ITO glass slide. After drying the sample at RT for 3 h, it was assembled on a conductive surface of a second electrode. The latter electrode surface was a circle with 2 mm diameter which was covered with nitrile butyl rubber as the dielectric. The ITO surface of the ITO glass slide was connected to the other electrode of a power source using a copper tape. The EL-assembly with the ground electrode was installed on a light microscope's stage and the ITO-glass slide was connected to the power source through a copper tape attached to the ITO surface. The capturing process was followed as described in example 7.

Example 11—EL Imaging of Multiplexed Immunohistochemical Double Stained Tissue The steps for labeling rabbit-anti mouse IgG secondary antibody with MPA capped Mn-doped ZnS was followed by the method described in example 3. The other nanoparticles were MPA-capped Cu-doped ZnS having an emission about green color wavelength.

The steps for preparation of electroluminescent NPs-Ab are described herein. 30 µL of MPA-capped Cu-doped ZnS nanoparticles (37 nm particle size, 10 mg/mL) were suspended in deionized (DI) water (1 ml) to form a suspension. 21 µL of EDC (30 µg/mL in DI water) was added to the suspension and the suspension was mixed for 1 min at RT. After 1 min, 5 µL of NHS (260 µg/ml in DI water) was added to the suspension. The suspension was incubated for 15 min at RT. Then 2 µL of 2-mercaptoethanol (2ME, Aldrich, 1:1000 VN solution in DI water) was added to the suspension to make a reaction mixture. 25 µl of goat-anti rabbit IgG antibody fraction (Sec Ab, Invitrogen, 2 mg/mL) was added to the reaction mixture and the reaction mixture was incubated for 2 h at RT. Reaction mixture was centrifuged at 14000 RPM for 10 min and the supernatant was decanted. For purification, the precipitates were re-dispersed in PBS and centrifuged again at 14000 RPM for 10 min and the supernatant was decanted. The purification step was repeated 3 times. After the last purification step, the precipitates were dispersed in 1 mL of PBS.

Tissue ITO-glass slide was prepared as described in example 1. Primary antibody, rabbit-anti CD34 antibody which is also reactive to the sheep endothelial cells in tissue, was incubated on the tissue ITO-glass slide for 1 h at RT, followed by washing with wash buffer made from 0.05% Tween 20 in PBS (0.1 M) for 5 min, afterward, 15 min washing with PBS (0.1M). Unoccupied surface markers on the tissue were blocked using BSA (1% w/v) incubated for 1 h at RT, then washed with wash buffer for 5 min and PBS for 10 min. Labeled secondary antibodies were incubated on the tissue ITO glass slide for 1 h at RT, followed by washing with wash buffer for 15 min and PBS for another 15 min. After drying the sample at RT for 3 h, it was assembled on a conductive surface of a metal electrode having a 2 mm diameter circular face which was covered with nitrile butyl rubber as the dielectric.

The ITO surface of the ITO glass slide was connected to the other electrode of a power source using a copper tape. The EL-assembly was installed on a light microscope's stage and the ITO-glass slide was connected to the power source through a copper tape attached to the ITO surface. The capturing process was followed as described in example 7.

Example 12 with Reference to FIG. 3—EL—Imaging Using Nonconductive Coverslip with Liquid Electrode In an alternative to the embodiment described in example 8, a tissue specimen 301 was mounted on a conventional glass coverslip 302 in place of the ITO glass coverslip with liquid electrode. As described above the liquid droplet 307 serves to electrically couple the EL assembly to the microscope body 306.

Example 13—EL—Unstained Tissue in Contact with Dielectric

A ready-to-use EL-assembly was prepared consisting of an ITO-glass slide pre-coated with electroluminescent material and covered with dielectric layer at point of use. By putting a slice of a fresh unstained tissue specimen on the EL-assembly a rapid live image can be obtained of cells within the tissue and their exposed compartment. This system saves significant operator hands-on time and manpower.

Figure 4:
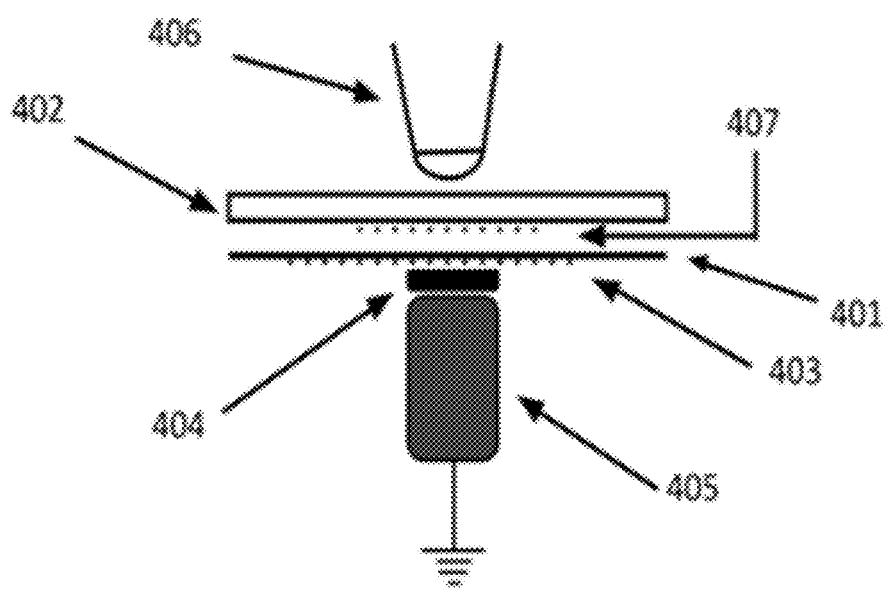
FIG. 4 is a schematic diagram describing an example embodiment of a system for electroluminescence characterization of a biological specimen where an electroluminescent assembly is prepared comprising two separate EL materials.

Example 14 with Reference to FIGS. 4 and 8—EL-Imaging of Different Levels of Generally Stained Cardiac Tissue with Two Different EL Materials An ITO-glass slide was evenly coated with 0.1% A mol Cu-doped ZnS nanoparticles using the method described in example 5.

A 5 µm thickness of paraformaldehyde-fixed sheep cardiac tissue 401 was mounted on the ITO surface of the ITO-glass slide 402 through using the method of example 1. The tissue was then stained by the procedure in example 2 so that a layer of Mn-doped ZnS 403 was placed on the tissue. The EL-assembly was prepared from the counterstained ITO-glass slide having a second layer of Cu-doped ZnS 407 with stained tissue, mounted on a dielectric layer made of nitrile butyl rubber on top of a metallic cylinder.

Figure 8A:
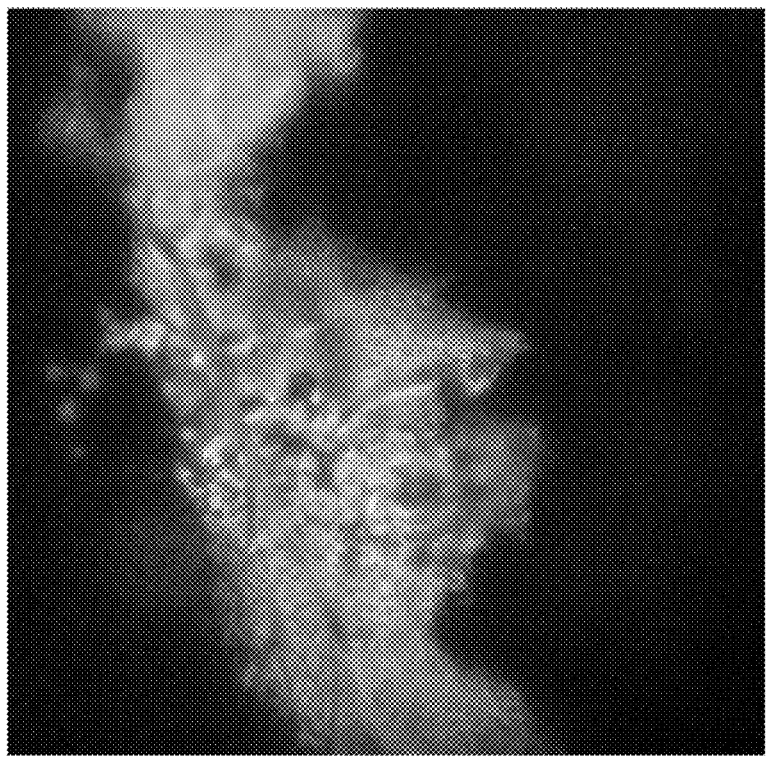
FIGS. 8A-8B depict photographic images of a section of cardiac tissue at different depths as described in example 14.
Figure 8B:
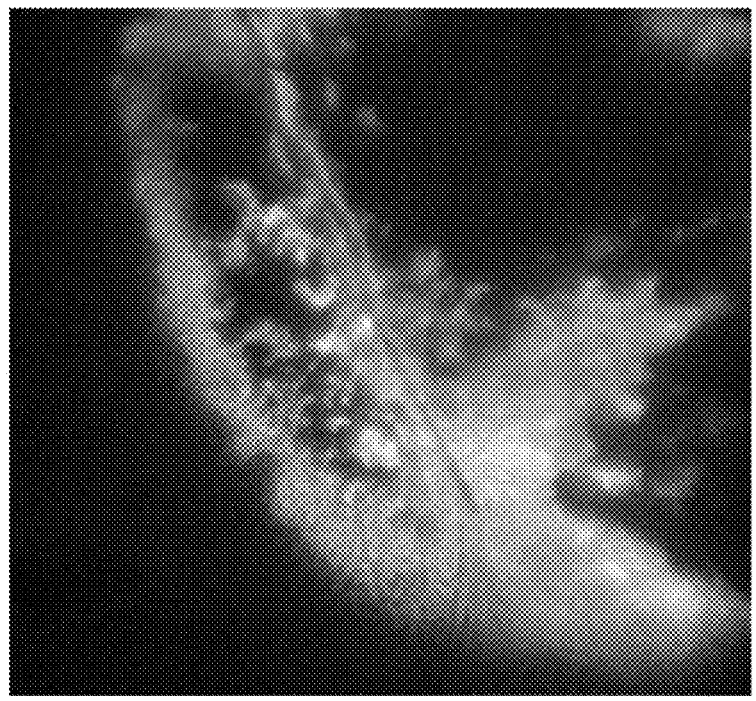

At closest distance between ITO surface of the ITO glass and the dielectric layer 404 residing on electrode 405, which means the distance is close to 5 um, thickness of the tissue slice, plus the thickness of the dielectric layer, the majority of the emission observed was the green emission of Cu-doped ZnS. Relatively less light was observed from the orange emitting nanoparticle close to the ITO surface. By bringing up the ITO-glass slide by about 2 µm, the other layer inside the 5 µm thickness tissue emitted orange light which showed around a lumen of a capillary blood vessel. By bringing up the ITO-glass slide by another 2 µm to add 4 µm totally to the distance between the tissue contains nanoparticles and the dielectric layer, the other layer of the tissue emitted orange light which shows the outer body of the capillary blood vessel which was totally dark, unexcited in the other levels. FIGS. 8A and 8B depict photographic images at different depth taken under these conditions.

Figure 7:
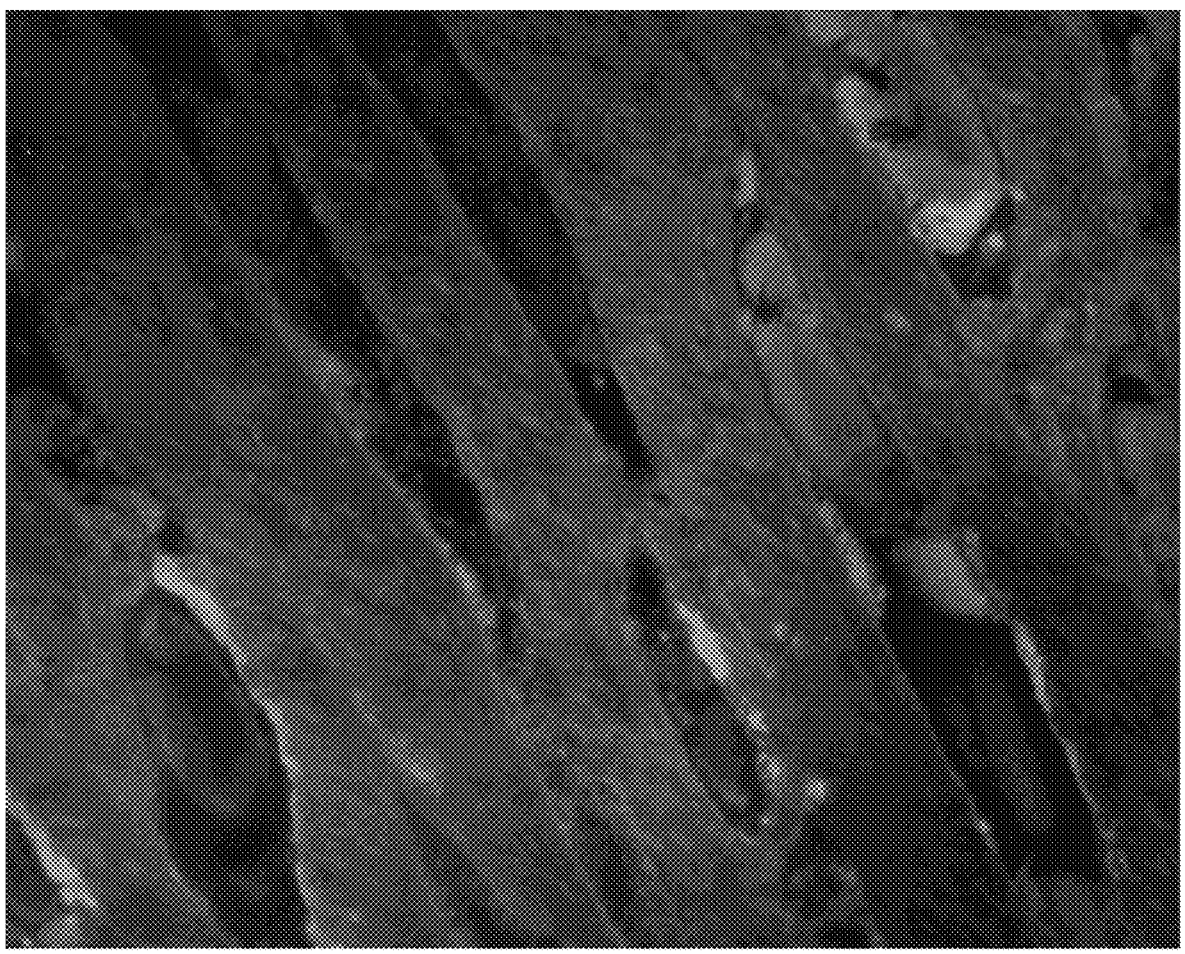
FIG. 7 is a photographic image of a section of cardiac tissue with fluorescence and electroluminescence excitation as described in example 15.

Example 15 EL-Imaging of Stained Cardiac Tissue on ITO Glass with Photoluminescence Co-Excitation Element An ITO-glass slide was evenly coated by (1% mol) Mn-doped ZnS nanoparticles using the method described in example 5. A 5 µm thickness of paraformaldehyde fixed sheep cardiac tissue then was mounted on the ITO surface of the ITO-glass slide by the method of example 1 and remained unstained. Then to make an EL-assembly, a copper tape was connected to the ITO surface of the ITO glass slide as shown in FIG. 1. The unstained tissue on ITO glass was mounted on a dielectric layer made of a thin layer (<1 mm) of nitrile butyl rubber which was attached to the face of a metal cylindrical electrode (2 mm diameter). The metallic cylinder was connected to the power source which produced 2500 Vp-p at 35 kHz. The energized wire of the power source was connected to the copper tape. The EL assembly sandwiched between the two electrodes was mounted on a fluorescent microscope which was equipped with a CCD color camera. The EL image was captured for 3 s at 100× magnification, energizing the EL assembly which was also the exposure time for the camera shutter. The EL image in combination of PL excitation was captured by using a long pass filter cube with blue light excitation and dichroic barrier for 450 nm and emission pass longer than 475 nm. The co-excited image was captured at 100× magnification, 3 s energizing the EL assembly along with blue light. A representative image is shown in FIG. 7.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for characterizing a biological specimen comprising:
    applying a biological specimen to a dielectric layer;
    preparing an electroluminescent assembly comprising:
        a biological specimen in contact with the dielectric layer,
        a quantity of an electroluminescent material, and
        a substrate;
    positioning the electroluminescent assembly between a pair of electrodes;
    transmitting an electrical signal from a power source through the pair of electrodes to the electroluminescent assembly thereby producing electroluminescence;
    capturing the electroluminescence;
    determining characteristics of the biological specimen in response to the electroluminescence; and
    relating properties of the electroluminescence to the characteristics of the biological specimen,
    wherein the electroluminescent material is irreversibly associated with an affinity binding substance that is specifically bindable with a target substance in the biological specimen and thereby indicates the presence, amount, or location of the target substance in the biological specimen.

2. The method of claim 1 wherein the substrate is transparent.

3. The method of claim 1 wherein the electroluminescent assembly serves as one of the pair of electrodes.

4. The method of claim 1 wherein the electroluminescent material comprises particles.

5. The method of claim 4 wherein the particles are comprised of a material selected from the group consisting of semiconductor particles, doped semiconductor particles, elemental Si particles, elemental Ge particles, quantum dots, fluorescent monomers, fluorescent oligomers, fluorescent polymers, phosphorescent monomers, phosphorescent oligomers, phosphorescent polymers and mixtures thereof.

6. The method of claim 4 wherein the particles are comprised of zinc sulfide nanocrystals doped with a transition metal.

7. The method of claim 5 wherein the particles are comprised of two or more types of particles and each of the two or more types of particles emits light of a different color.

8. The method of claim 1 wherein the electrical signal is a direct current signal.

9. The method of claim 1 wherein the electrical signal is a time-varying electrical signal.

10. The method of claim 1 wherein the electrical signal is an alternating current signal.

11. The method of claim 1 wherein the electroluminescent assembly remains at open circuit in relation to the power source.

12. The method of claim 1 wherein the biological specimen is selected from the group consisting of cells, tissues, viruses, capsids, and cellular components, the cellular components are selected from the group consisting of cellular nuclei, nucleic acids, mitochondria, antigenic proteins, and receptors.

13. The method of claim 1 wherein the characteristics of the biological specimen are selected from the group consisting of morphology, topology, cell margins, shape, intercellular spaces, and the presence, amount, or location of affinity binding substances.

14. The method of claim 1 wherein the electroluminescence is captured using a microscope.

15. The method of claim 1 wherein the relating properties of the electroluminescence to the characteristics of the biological specimen comprises locating cell boundaries, identifying different cell types, or assessing the 3D topology of the biological specimen.

16. The method of claim 1 wherein the dielectric layer is interposed between the biological specimen and the electroluminescent material.

17. The method of claim 1 wherein the biological specimen contacts the substrate in the electroluminescent assembly.

18. The method of claim 1 wherein the electroluminescent material exists as a layer applied onto a surface of the substrate within the electroluminescent assembly.

19. The method of claim 1 further comprising
irradiating the biological specimen with a light source to produce photoluminescence and capturing the photoluminescence.

20. A method for characterizing a biological specimen comprising:
applying a biological specimen to a dielectric layer;
preparing an electroluminescent assembly comprising:
a biological specimen in contact with the dielectric layer,
a quantity of an electroluminescent material, and
a substrate;
positioning the electroluminescent assembly between a pair of electrodes;
transmitting an electrical signal from a power source through the pair of electrodes to the electroluminescent assembly thereby producing electroluminescence;
capturing the electroluminescence;
determining characteristics of the biological specimen in response to the electroluminescence; and
relating properties of the electroluminescence to the characteristics of the biological specimen,
wherein the relating properties of the electroluminescence to the characteristics of the biological specimen comprises measuring the location, distribution, or number of a target substance in the biological specimen based on a pattern and intensity of the electroluminescent signal.

21. The method of claim 20 wherein the substrate is transparent.

22. The method of claim 20 wherein the electroluminescent assembly serves as one of the pair of electrodes.

23. The method of claim 20 wherein the electroluminescent material comprises particles.

24. The method of claim 23 wherein the particles are comprised of a material selected from the group consisting of semiconductor particles, doped semiconductor particles, elemental Si particles, elemental Ge particles, quantum dots, fluorescent monomers, fluorescent oligomers, fluorescent polymers, phosphorescent monomers, phosphorescent oligomers, phosphorescent polymers and mixtures thereof.

25. The method of claim 23 wherein the particles are comprised of zinc sulfide nanocrystals doped with a transition metal.

26. The method of claim 24 wherein the particles are comprised of two or more types of particles and each of the two or more types of particles emits light of a different color.

27. The method of claim 20 wherein the electrical signal is a direct current signal.

28. The method of claim 20 wherein the electrical signal is a time-varying electrical signal.

29. The method of claim 20 wherein the electrical signal is an alternating current signal.

30. The method of claim 20 wherein the electroluminescent assembly remains at open circuit in relation to the power source.

31. The method of claim 20 wherein the biological specimen is selected from the group consisting of cells, tissues, viruses, capsids, and cellular components, the cellular components are selected from the group consisting of cellular nuclei, nucleic acids, mitochondria, antigenic proteins, and receptors.

32. The method of claim 20 wherein the characteristics of the biological specimen are selected from the group consisting of morphology, topology, cell margins, shape, intercellular spaces, and the presence, amount, or location of affinity binding substances.

33. The method of claim 20 wherein the electroluminescence is captured using a microscope.

34. The method of claim 20 wherein the relating properties of the electroluminescence to the characteristics of the biological specimen comprises locating cell boundaries, identifying different cell types, or assessing the 3D topology of the biological specimen.

35. The method of claim 20 wherein the dielectric layer is interposed between the biological specimen and the electroluminescent material.

36. The method of claim 20 wherein the biological specimen contacts the substrate in the electroluminescent assembly.

37. The method of claim 20 wherein the electroluminescent material exists as a layer applied onto a surface of the substrate within the electroluminescent assembly.

38. The method of claim 20 further comprising irradiating the biological specimen with a light source to produce photoluminescence and capturing the photoluminescence.

39. A device to characterize an electroluminescent assembly having of a biological specimen in contact with a dielectric layer, a quantity of an electroluminescent material, and a substrate, the device comprising:
a power source,
a pair of electrodes operably coupled to the power source, at least one electrode of the pair of electrodes is transparent, and
an optical device;
wherein the power source is configured to supply power to the electroluminescent assembly via the pair of electrodes;
wherein the power source is configured to cause the electroluminescent assembly to produce electroluminescence;
wherein one or more properties of the electroluminescence are determined by the characteristics of the electroluminescent assembly; and
wherein the optical device is configured to capture the electroluminescence from the electroluminescent assembly through the at least one transparent electrode of the pair of electrodes,
wherein the optical device is a fluorescence microscope,
wherein a light source in the fluorescence microscope produces a photoluminescence signal from the biological specimen in addition to electroluminescence signal from the electroluminescent material and the optical device captures both the photoluminescence and electroluminescence signals.

40. The device of claim 39 wherein the power source is configured to produce a constant electrical signal.

41. The device of claim 39 wherein the power source is configured to produces a time-varying electrical signal.

42. The device of claim 39 wherein at least one of the electrodes is a transparent glass or plastic electrode.

43. The device of claim 39 wherein both of the pair of electrodes are transparent.

44. A system for characterizing a biological specimen comprising the device of claim 39 and an electroluminescent assembly having a biological specimen in contact with a dielectric layer, a quantity of an electroluminescent material, and a substrate.

45. A device to characterize an electroluminescent assembly having of a biological specimen in contact with a dielectric layer, a quantity of an electroluminescent material, and a substrate, the device comprising:
a power source,
a pair of electrodes operably coupled to the power source, at least one electrode of the pair of electrodes is transparent, and
an optical device;
wherein the power source is configured to supply power to the electroluminescent assembly via the pair of electrodes;
wherein the power source is configured to cause the electroluminescent assembly to produce electroluminescence;
wherein one or more properties of the electroluminescence are determined by the characteristics of the electroluminescent assembly; and
wherein the optical device is configured to capture the electroluminescence from the electroluminescent assembly through the at least one transparent electrode of the pair of electrodes,
wherein the optical device is a fluorescence microscope,
wherein a light source in the fluorescence microscope produces a photoluminescence signal from the electroluminescent material in addition to electroluminescence signal from the electroluminescent material and the optical device captures both the photoluminescence and electroluminescence signals.

46. The device of claim 45 wherein the power source is configured to produce a constant electrical signal.

47. The device of claim 45 wherein the power source is configured to produce a time-varying electrical signal.

48. The device of claim 45 wherein at least one of the electrodes is a transparent glass or plastic electrode.

49. The device of claim 45 wherein both of the pair of electrodes are transparent.

50. A system for characterizing a biological specimen comprising the device of claim 45 and an electroluminescent assembly having a biological specimen in contact with a dielectric layer, a quantity of an electroluminescent material, and a substrate.

* * * * *